(12) United States Patent
Contreras et al.

(10) Patent No.: US 7,910,221 B2
(45) Date of Patent: Mar. 22, 2011

(54) BIOCOMPATIBLE TITANIUM ALLOYS

(75) Inventors: Ramiro Contreras, Del Mar, CA (US); Herman Sahlin, Göteborg (SE); John A. Frangos, La Jolla, CA (US)

(73) Assignee: La Jolla Bioengineering Institute, San Diego, CA (US)

( * ) Notice: Subject to any disclaimer, the term of this patent is extended or adjusted under 35 U.S.C. 154(b) by 447 days.

(21) Appl. No.: 11/672,867

(22) Filed: Feb. 8, 2007

(65) Prior Publication Data

US 2007/0191944 A1 Aug. 16, 2007

Related U.S. Application Data (60) Provisional application No. 60/771,600, filed on Feb. 8, 2006.

(51) Int. Cl.
*A61F 2/02* (2006.01)
(52) U.S. Cl. ..... 428/472; 428/386; 428/701; 623/11.11; 623/23.56; 623/1.44
(58) Field of Classification Search .......... None
See application file for complete search history.

(56) References Cited

U.S. PATENT DOCUMENTS

| | | | |
|---|---|---|---|
| 4,846,834 A | 7/1989 | von Recum et al. | |
| 5,385,662 A | 1/1995 | Kurze et al. | |
| 5,468,562 A | 11/1995 | Farivar et al. | |
| 6,613,088 B1 | 9/2003 | Babizhayev | |
| 6,808,613 B2 | 10/2004 | Beauvir | |
| 6,869,701 B1 * | 3/2005 | Aita et al. | 428/698 |
| 2002/0170593 A1 * | 11/2002 | Yadav et al. | 136/261 |
| 2002/0172826 A1 * | 11/2002 | Yadav et al. | 428/402 |
| 2003/0012953 A1 * | 1/2003 | Yadav et al. | 428/402 |
| 2003/0013319 A1 * | 1/2003 | Holmes et al. | 438/761 |
| 2004/0180203 A1 * | 9/2004 | Yadav et al. | 428/402 |
| 2005/0074602 A1 | 4/2005 | Bjursten et al. | |

OTHER PUBLICATIONS

P.C.S. Hayfield. Development of a New Material-Monolithic Ti4O7 Ebonex Ceramic. MFIS Ltd, 2002, 97 p.*
N. Aukland et al. J. Mater. Res. vol. 19, No. 6, Jun. 2004, 1723-1729.*
N. Chan et al. J. Electrochem. Soc. Aug. 1981, 1762-1769.*
W. Lo et al. Surface Science, 71, 1978 199-219.*

* cited by examiner

*Primary Examiner* — Jennifer C McNeil
*Assistant Examiner* — Vera Katz (57) ABSTRACT

Methods and compositions are disclosed for coating a biocompatible medical implant with a surface layer having antioxidant activity. In various embodiments, a surface layer described herein destroys the oxidative activity of a reactive oxygen species (ROS) upon contact. An ROS can be, for example, an ROS generated by neutrophils in vivo. In various embodiments, a surface layer comprises a titanium oxide layer that can comprise a rutile, an anatase or a perovskite crystal structure, and can include defects comprising Ti(III). In some embodiments, the oxide layer can further comprise a dopant such as niobium. In some embodiments, methods for forming a surface layer on a biocompatible medical implant having antioxidant activity are disclosed.

7 Claims, 6 Drawing Sheets

BIOCOMPATIBLE TITANIUM ALLOYS

CROSS-REFERENCE TO RELATED APPLICATIONS

This application claims priority to U.S. Provisional Patent Application 60/771,600 filed Feb. 8, 2006, which is hereby incorporated by reference in its entirety.

STATEMENT REGARDING FEDERALLY SPONSORED RESEARCH OR DEVELOPMENT

This invention was made in part with Government support under National Institutes of Health Grants EB000823, and AR47032. The Government has certain rights in the invention.

FIELD

The present teachings relate to materials with biocompatibility properties for use as medical implants and for the storage and culturing of medical samples.

INTRODUCTION

Titanium and some titanium alloys exhibit good biocompatibility when used as materials for medical implants and devices. However, implants coated with or composed of titanium or some titanium alloys can still provoke an inflammatory response.

Titanium is a biomaterial that exhibits good biocompatibility and evokes minimal inflammatory response following implantation. Titanium and its alloys have been used as biomaterials due to their biocompatibility properties (Wang, K., Materials Science & Engineering A-Structural Materials Properties Microstructure & Processing, 1996. 213(1-2): p. 134-7. Early studies observed that titanium bone implants in animals are well accepted when compared to other metals, and titanium is used extensively in restorative surgery, particularly as a bone-anchoring and joint-replacement material. Other studies have shown that titanium evokes less tissue reaction in rabbit muscle as compared to other metals. To increase the choices when selecting biomaterials for the needs of a particular implant, investigators have used metallization of polymeric implants or have modified the surface of titanium and its alloys to increase wear-resistant properties (U.S. Pat. No. 5,468,562 to Farivar et al.; WIPO patent application WO99474716 of Olsson et al.). Metal alloy biomaterials used for implants include titanium alloys, cobalt-chromium-molybdenum alloys, cobalt-chromium-tungsten-nickel alloys and non-magnetic stainless steels (300 series stainless steel). See, e.g., U.S. Pat. No. 4,775,426 to Murley et al. Such materials still produce a significant immune response, however, often necessitating immune-suppressive drugs having formidable side effects. Although titanium is widely used as an implant material, the mechanisms of its superior biocompatibility are presently unknown. Although $TiO_2$ is a good biocompatible material, it still provokes a significant inflammatory response.

$TiO_2$ can act as a catalyst in reactions involving reactive oxygen species. Crystalline $TiO_2$ powder can be used as a photocatalyst for the purification of water. Hydroxyl radicals that initiate oxidation of hydrocarbons to carbon dioxide, water and water-soluble organics are involved in these reactions. Such findings indicate that titanium oxide can act as a catalyst in reactions involving free radical species (Suzuki, R., and Frangos, J. A., Clinical Orthopaedics and Related Research 372: 280-289, 2000).

Implanted biomaterial devices can be seen as foreign bodies by the immune system, and can elicit an inflammatory response. See Gristina, A. G., Clinical Orthopaedics and Related Research 298: 106-118, 1994. This response is evidenced by the increased activity of macrophages, granulocytes, and neutrophils, which attempt to remove the foreign object by the secretion of degradative enzymes and free radicals like superoxide anion to inactivate or decompose the foreign object. Woven dacron polyester, polyurethane, velcro, polyethylene, and polystyrene were shown to elicit superoxide production from neutrophils by Kaplan, S. S., et al, J. Bio. Mat. Res. 26: 1039-1051, 1992.

The reaction of titanium metal with reactive oxygen species has long been recognized (Williams, D. F., J. Med Eng Technol. 1:195-198, 1977; Sundgren J-E, et al., J. Colloid Interface Sci. 110: 9-20, 1986; Tengvall, P. et al., Clin Mater. 9: 115-134, 1992). It has been observed that implanted titanium metal is readily corroded, leading to reaction products which include soluble $TiO_2(aq)$, $TiO_2^-$ and $TiO_2^{2-}$, Ti-superoxide and Ti-peroxide, and Ti-peroxy gel (Tengvall, P. et al., Clin Mater. 9: 115-134, 1992). Such reaction products can accumulate in spite of the presence of a "passivating" $TiO_2$ surface layer, due to the diffusion of titanium and oxygen atoms through the oxide layer.

It has been previously demonstrated that crystalline $TiO_2$ promotes the breakdown of hydrogen peroxide, peroxynitrite, and superoxide (Tengvall, P. et al., Biomaterials 10: 166-175, 1989; Suzuki, R., et al. J. Biomed. Mater. Res. A 66: 396-402 2003; Sahlin, H., et al., J. Biomed. Mater. Res. A 77: 43-49 2006). It was speculated that the valence state of titanium plays a role in the degradation of ROS (Tengvall, P. et al., Biomaterials 10: 166-175, 1989; Sahlin, H., et al., J. Biomed. Mater. Res. A 77: 43-49 2006).

$TiO_2$, $BaTiO_3$, and $SrTiO_3$ are well known to have catalytic properties (Kowalski, J. M., and Tuller, H. L. Ceram. Intl. 7: 55-59 1981; Henrich V E., Rep. Prog. Phys. 48: 1481-1541, 1985. These surface properties depend on the surface chemical composition and electronic structure. Non-stoichiometric, or oxygen deficient, materials in general produce new electronic states that do not exist on a stoichiometric surface. Annealing at high temperatures reduces these materials through the production of oxygen vacancies (Chung, Y. W., et al., Surface Science 64: 588-602 1977; Henrich, V. E., et al., Phys. Rev. B 17: 4908-4021, 1978; Lo, W. J., et al., Surface Science 71: 199-219 1978). The removal of $O^{2-}$ ions leaves a net positive charge in the crystalline lattice, but in order to preserve charge neutrality two electrons are trapped by two adjacent Ti ions, changing their valence to +3. These surface defects are active sites for many catalytic reactions (Henrich, V. E., et al., Phys. Rev. B 17: 4908-4021, 1978; Henrich, V. E., Prog. Surf. Sci. 14: 175-199. 1983). Similarly, when $TiO_2$ or $SrTiO_3$ are doped with Nb, Ti atoms with a valence state of +3 are produced (Chan, N. H., et al., J. Electrochem. Soc. 128: 1762-1769, 1981; Aukland, N., et al., J. Mater. Res. 19: 1723-1729, 2004; Baumard. J. F., and Tani, E., J. Chem. Phys. 67: 857-860, 1977). For every $Nb^{5+}$ that is substituted for a $Ti^{4+}$ in the crystalline lattice, an adjacent atom of Ti is converted from +4 to +3 valence state in order to maintain electroneutrality. In addition, doping $TiO_2$ with Nb creates $Ti^{3+}$ sites without the generation of oxygen vacancies (Kowalski, J. M., Ceram. Intl. 7: 55-59, 1981). In addition, it has been reported that when $10M\ H_2O_2$ reacts with crystalline $TiO_2$ over a 1-week period, not only $O_2(g)$ but possibly other reaction product(s) such as Ti-peroxide (Tengvall, P., et al., Biomaterials 10: 166-175, 1989) is produced.

Macrophages produce both superoxide and nitric oxide when stimulated. Polymorphonuclear leukocytes produce superoxide after stimulation. Superoxide undergoes a rapid reaction with superoxide dismutase to form hydrogen peroxide. Superoxide dismutase has a critical role in regulating reactive oxygen species concentrations. This regulatory process appears to be compromised, however, in tissues surrounding polyester implants (Glowinski, J., et al., European surgical research, 29: 368-374, 1997. This is likely due to inactivation of the superoxide dismutase enzyme by the oxidative environment generated by the inflammatory response, thus compounding the deleterious accumulation of oxidant species in the vicinity of the implant.

In addition to superoxide, another reactive species, peroxynitrite, is a mediator in the inflammatory response. Peroxynitrite is formed by the reaction of superoxide with nitric oxide at near-diffusion limited rates which are several times faster than the reaction of superoxide with superoxide dismutase. Macrophages and cells from inflammatory exudates are suspected to produce peroxynitrite in vivo.

Peroxynitrite is a very reactive oxidant thought to play a role in inflammation. Clinical studies provide evidence that peroxynitrite is produced during inflammation. The blood serum and synovial fluid from patients with the inflammatory joint disease rheumatoid arthritis were found to contain 3-nitrotyrosine markers indicating peroxynitrite formation, while body fluids from normal patients contained no detectable 3-nitrotyrosine. Similarly, no 3-nitrotyrosine markers were detected in body fluids from patients with osteoarthritis, a largely non-inflammatory joint disease. Importantly, it has been reported that 3-nitrotyrosine markers for peroxynitrite were also observed at the interface membrane of hip implants suffering from aseptic loosening, which is characterized by local inflammation (Hukkanen, M., et al., The Journal of Bone & Joint Surgery (Br), 79: p. 467-474, 1997; Hukkanen, M., et al., Clinical Orthopaedics and Related Research, 352: 53-65, 1998).

Synthetic decomposition catalysts specific for peroxynitrite have been explored as a method of inhibiting damage induced by this potent reactive species (Misko, T. P., et al., The Journal of Biological Chemistry, 273: 15646-15653 1998). In addition, metalloporphyrin catalysts capable of breaking down peroxynitrite have been shown to have protective effects in animal models involving inflammatory states ranging from splanchinic artery occlusion and reperfusion, experimental autoimmune encephalomyelitis, endotoxin induced intestinal damage and carrageenan-induced paw-edema (Salvemini, D., et al., British Journal of Pharmacology 127: 685-692, 1999; Cuzzocrea, S., et al., FASEB Journal, 14: 1061-1072, 2000).

Titanium is capable of enhancing the breakdown and inhibiting the reactivity of peroxynitrite (Suzuki, R. and J. A. Frangos, Clinical Orthopaedics and Related Research, 372: p. 280-289, 2000). Titanium oxide can also inhibit the nitration reactions of peroxynitrite at physiological pH levels compared to polyethylene. Furthermore, implants in which the surface has been micropatterned with titanium oxide are able to break down peroxynitrite as effectively as when the entire surface is covered by titanium oxide (US Patent Application 20050074602 of Bjursten et al.).

The impact of continuous attempts by an organism to degrade biomaterial implants can lead to increased morbidity and device failure. In the case of polyurethane pacemaker lead wire coatings, this can result in polymer degradation and steady loss of function. In the use of synthetic vascular grafts, this results in persistent thrombosis, improper healing, and restenosis. Orthopedic devices such as hip and knee joints have a tendency for wear and build-up of fine debris resulting in a painful inflammatory response. In addition, the surrounding tissue does not properly heal and integrate into the prosthetic device, leading to device loosening and opportunistic bacterial infections. It has been proposed by many researchers that chronic inflammation at the site of implantation leads to the exhaustion of the macrophages and neutrophils, and an inability to fight off infection.

Because implants coated with or composed of titanium or some titanium alloys can still provoke an inflammatory response, there is a need for new biocompatible materials which provoke less of an inflammatory response than titanium or titanium alloys which are currently used to as biocompatible materials.

SUMMARY

The present teachings include biocompatible materials, as well as methods for forming a biocompatible materials which have more potent anti-oxidant properties the biocompatibility of medical implants. A biocompatible material, in some embodiments, can be comprised by a biomedical device such as a device that is implanted into a recipient. In some aspects, the biocompatible material can be comprised by the exposed surface of the device.

In some aspects, the present teachings set forth biocompatible implants which comprise a surface comprising a crystalline titanium oxide having defects comprising Ti(III). In some configurations, a surface can comprise a dopant. In various configurations, a dopant can have a +5 valence state, and can be a metal such as vanadium, niobium, tantalum, chromium, molybdenum, tungsten, manganese, rhenium, ruthenium, iridium, or a combination thereof. In some configurations, the dopant can be niobium.

In various aspects, the crystalline titanium comprised by a biocompatible material can comprise $TiO_2$, or can comprise a titanium alloy, such as an alloy of titanium oxide. In various configurations, the titanium alloy can be $SrTiO_3$ or $BaTiO_3$.

In yet other configurations, the titanium alloy can further comprise a dopant, such as vanadium, niobium, tantalum, chromium, molybdenum, tungsten, manganese, rhenium, ruthenium, iridium, or a combination thereof. In some aspects, the titanium alloy is niobium-doped $SrTiO_3$.

In yet other aspects of the present teachings, a crystalline titanium oxide comprised by biocompatible implant can comprise a perovskite crystal structure, an anatase crystal structure or a rutile crystal structure.

In some configurations, the biocompatible implant can comprise a biocompatible material which comprises two or more layers. In some embodiments, one layer can comprise titanium metal or a titanium oxide, while an additional layer can include doped titanium or doped titanium oxide.

In yet other aspects of the present teachings, the inventors herein disclose methods of increasing anti-oxidant activity in a biocompatible material. These methods include coating an implant, such as a medical implant, with a biocompatible surface. In various embodiments, the method comprises subjecting a surface comprising titanium to anodic spark deposition (ASD). In various aspects, a surface produced using ASD can break down an reactive oxygen species (ROS) such as peroxynitrite, superoxide or peroxide at a rate greater than that of the surface prior to the anodic spark deposition.

In various configurations, the surface comprising titanium can further comprise a dopant, such as vanadium, niobium, tantalum, chromium, molybdenum, tungsten, manganese, rhenium, ruthenium, iridium, or a combination thereof. In some embodiments, the surface can further comprise niobium, while in other embodiments, a surface can comprise a titanium oxide. In various aspects, titanium oxide comprised a surface following ASD can further comprise at least one metal, such as, for example, barium and/or strontium.

In yet other aspects, the surface can comprise a perovskite titanate following ASD. Furthermore, in some configurations, a perovskite titanate of these embodiments can further comprise a dopant, such as, for example, vanadium, niobium, tantalum, chromium, molybdenum, tungsten, manganese, rhenium, ruthenium, iridium, or a combination thereof. In certain aspects, the dopant of these aspects can be niobium.

In yet other aspects of these methods, a surface remaining after ASD can comprise a titanate such as, without limitation, a rutile titanate, an anastase titanate and a combination thereof.

In some embodiments, methods for coating an implant can include depositing titanium and at least one other metal on the surface of a biocompatible medical implant to form a surface of the implant, wherein the surface comprises the titanium and the metal. The implant surface can then be subjected to ASD, whereby the deposited metals adopt rutile crystal structures, anatase crystal structures or a combination thereof.

In yet other embodiments, a method is disclosed for coating a biocompatible implant with a perovskite titanate. In various configurations, these methods can comprise depositing a titanium metal alloy on the surface of the implant to form a second surface overlaying the surface of the implant, and oxidizing the second surface by ASD in the presence of an electrolyte. A perovskite titanate can form when the electrolyte is a cation-donating electrolyte, such as, for example and without limitation, barium hydroxide or calcium hydroxide.

In other aspects of the methods, titanium can be deposited on the surface of an implant along with rare earth element metal.

In yet other aspects of the methods, titanium can be deposited on the surface of an implant along with an actinide metal or a lanthanide metal.

In yet other aspects of the methods, titanium can be deposited on the surface of an implant along with another metal such as vanadium, niobium, tantalum, chromium, molybdenum, tungsten, manganese, rhenium, ruthenium and iridium.

In still other aspects, methods are disclosed for increasing the biocompatibility of an implant. These methods comprise establishing a titanium oxide coating on the surface of the implant by anodic spark deposition, thereby causing the crystals of titanium oxide to adopt a rutile structure, and anatase structure, or a combination thereof.

In yet another embodiment, methods for increasing the biocompatibility of an implant are disclosed. These methods comprise establishing an electron doped titanium oxide coating on the surface of the implant by anodic spark deposition such that the crystals comprising said electron doped titanium oxide coating adopt a rutile or anatase structure.

In yet another embodiment of the present teachings, methods for increasing the biocompatibility of an implant are disclosed. These methods comprise establishing an electron doped perovskite titanate coating on the surface of the implant.

In yet other embodiments of the present teachings, biomedical implant surfaces are disclosed having a perovskite titanate coating. A perovskite titanate of these embodiments can include titanates such as, without limitation, calcium titanate, strontium titanate, barium titanate, yttrium titanate or a combination thereof.

In yet another embodiment, a surface is disclosed which comprises titanium alloyed with another element, which may be, without limitation, a metal such as vanadium, niobium, tantalum, chromium, molybdenum, tungsten, manganese, rhenium, rhodium iridium or a combination thereof.

In still another embodiment, a titanium alloy surface is disclosed which is formed by anodic spark deposition in the presence of an electrolyte, and wherein the surface adopts a perovskite crystal structure.

In still another embodiment, a titanium alloy surface is disclosed comprising an electron doped perovskite crystal structure. Such a surface can be formed by anodic spark deposition in the presence of an electrolyte.

In still another embodiment, a titanium metal alloy surface is disclosed comprising crystals of an anatase or rutile structure. Such a surface can be formed by oxidation using anodic spark deposition.

In yet another embodiment, a titanium metal alloy surface is disclosed comprising a perovskite crystal structure. Such surfaces can be formed by oxidation using anodic spark deposition in the presence of an electrolyte which can contribute to the perovskite structure.

In still another embodiment, a biomaterial is disclosed, wherein the biomaterial is composed of titanium, and the surface of the biomaterial is coated by a layer of titanium oxide deposited by anodic spark deposition.

In yet another embodiment, a biomaterial is disclosed, wherein the biomaterial has a surface comprising metals adopting a perovskite crystal structure.

In yet another embodiment, a biomaterial is disclosed which comprises a titanium metal alloy at least 50% by weight. A biomaterial comprising a titanium metal alloy at least 50% by weight includes a biomaterial which comprises a titanium metal alloy at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% by weight, or a titanium metal alloy 100% by weight.

These and other features, aspects and advantages of the present teachings will become better understood with reference to the following description, examples and appended claims.

BRIEF DESCRIPTION OF THE DRAWINGS

The signals were normalized to that of the quartz sample. The brackets indicate significant difference ($p<0.05$) between groups. Both $BaTiO_3$ and niobium (Nb) doped $SrTiO_3$ reduces the concentration of peroxynitrite better than $TiO_2$.

DETAILED DESCRIPTION

Abbreviations and Definitions

To facilitate understanding of the present disclosure, a number of terms and abbreviations as used herein are defined below as follows:

Alloy: As used herein, the term "alloy" refers to a mixture comprising two or more metals. The term is not limited to purely metallic alloys—i.e., an alloy can also include other elements and/or impurities, such as, for example, oxygen.

Titanium metal alloy: As used herein, the term "titanium metal alloy" refers to a mixture comprising titanium and at least one other metal. A titanium metal alloy can further comprise other elements and/or impurities, such as, for example, oxygen.

Electrolyte: As used herein, the term "electrolyte" refers to a substance that, in solution or in molten form, conducts electricity.

Biomaterial: As used herein, the term "biomaterial" includes a material used to construct artificial tissue, organs, rehabilitation devices, or prostheses to replace or supplement natural body tissues, and which induces an inflammatory response within a therapeutically acceptable level when contacted with a body tissue, including no inflammatory response.

Biocompatible: As used herein, the term "biocompatible" refers to the ability of a material to perform with appropriate host response in a specific application. The term "biocompatible implant" includes an implant that is accepted by the body with little or no immune or other inflammatory response.

Implant: As used herein, the term "implant" includes an artificial device which replaces, supplements, enhances, substitutes for and/or acts as a missing biological structure.

Anode: As used herein, the term "anode" refers to the positive electrode in an electrolytic system or circuit. The anode is where oxidation occurs, and the term also refers to the negative discharge plate in an electrochemical cell. The term anode is further characterized by the property that in solution, negative ions will flow to the anode.

Cathode: As used herein, the term "cathode" refers to the negative electrode in an electrolytic system or circuit. The cathode is where reduction occurs, and the term also refers to the positive discharge plate in an electrochemical cell. The term cathode is further characterized by the property that in solution, positive ions will flow to the cathode.

Anodic spark deposition: As used herein, the term "anodic spark deposition" includes oxidation reactions occurring at voltages close to, at or above the dielectric breakdown point of the metal serving as the cathode in the oxidation process. In the process of anodic spark deposition, an oxide layer continues to grow as long as it is under an electric field strong enough to drive the ions through the layer. At the breakdown voltage, defects, areas of concentrated stress and non-uniform thickness in the film are randomly spread throughout the surface of the oxide layer, making the potential voltage drop across the surface non-uniform. When the applied potential is further increased, the voltage drop at these weak points exceeds the dielectric strength of the layer. An extremely high concentration of current flows through these small areas at which time sparks can often be seen across the surface. Anions are strongly attracted by the high intensity of the electric discharge at the metal-anodic interface, resulting in an acceleration of deposition of material through the sparking process. During the process of anode spark deposition, the temperature can be greater than the melting temperature of the metal.

Oxidize: As used herein, the term "oxidize" refers to the process by which an atom loses an electron.

Electrolytic cell: As used herein, the term "electrolytic cell" includes a composition of materials that under the influence of electricity causes a redox reaction to occur. In an electrolytic cell, the positively charged anode is paired with the positively charged end of a voltaic cell, and the negative cathode is paired with the negative end of a voltaic cell, thus reversing the flow of electrons from the standard pathway of negative to positive (such as in a voltaic cell), to positive to negative.

Dielectric breakdown voltage: As used herein, the term "dielectric break-down voltage" refers to the voltage at which a dielectric material will begin to conduct current.

Perovskite: As used herein, the term "perovskite" includes oxides having the same crystalline structure as the mineral, $CaTiO_3$, which is usually expressed as $ABO_3$. An ideal perovskite has a structure in which A (cation) is located at the center of the cubic unit cell, B (cation) is located at each corner and 0 (anion) is located at the center of each side.

Doped/doping: As used herein, the terms "doped" and "doping" refer to the process of introducing impurities to a substance to increase its conductive properties.

Dopant: At used herein, the term "dopant" refers to an impurity introduced into a substance at less than stoichiometric amounts, to confer a property to the substance. A dopant can be introduced into a substance at an amount of less than about 1% at. wt.

The present inventors disclose herein interactions between reactive oxygen species (ROS) and titanate crystals such as $TiO_2$, $SrTiO_3$, and $BaTiO_3$.

The present teachings describe biocompatible implants comprising a surface comprising a crystalline titanium oxide having defects comprising Ti(III). The present inventors have found that when defects and impurities are added to titanate crystals such as $TiO_2$ and $SrTiO_3$, the ability to degrade reactive oxygen species (ROS) is enhanced.

Without being limited by theory, such defects are believed to serve as catalytic sites which can destroy reactive oxygen species (ROS), such as, for example, peroxides (e.g., hydrogen peroxides), superoxides and peroxynitrates. Furthermore, such defects are believed to promote a change in the valence state of titanium while maintaining the original crystal structure. Among the oxidative species which can be destroyed using the titanate crystals of the present teachings are ROS found in biological systems, such as, for example, oxidants produced by neutrophils at inflammation sites. Accordingly, the introduction of such defects to a coating of a biocompatible implant can reduce tissue reactions. Since we hypothesized that surface defects can be the active sites for the catalytic reaction, increasing their density should have increased the amount of ROS catalyzed. Consistent with this hypothesis, the annealed samples in vacuum to produce a greater density of oxygen defects and therefore an increased density of $Ti^{3+}$ sites, enhancing the degradation of ROS. The reverse was also shown to be true: reannealing the reduced samples at 950 C in air can decrease the efficiency of ROS degradation. It is believed that this effect results from filling oxygen vacancies. In addition, ROS generated by both SIN-1 and neutrophils were degraded at a significantly greater rate on Nb-doped $TiO_2$ surfaces in comparison to undoped $TiO_2$ surfaces. In addition, without being limited by theory, the present inventors have shown that the antioxidant properties of titanate oxides depend on the concentration of Ti(III) sites. This was evident with crystalline surfaces that were vacuum annealed, producing higher concentrations of Ti(III) defects, and then reannealed to decrease the concentration of oxygen vacancies, thus lowering the concentration of Ti(III). In some embodiments of the present teachings, the inventors find that a more effective method of introducing Ti(III) is by doping $TiO_2$ and $SrTiO_3$, with Nb. The addition of Nb creates the same defects but without the creation of oxygen vacancies. Hence, in various aspects, Nb-doped $TiO_2$ and $SrTiO_3$ comprise a novel class of biomaterials or biomaterial coatings which have superior antioxidant properties.

In some embodiments of the present teachings, the inventors have found that active sites comprising $Ti^{3+}$ can be generated in other transition metal oxides. In some aspects, $SrTiO_3$ can have a perovskite cubic crystal structure with cations Sr and Ti having valence states +2 and +4, respectively. Similar to $TiO_2$, $SrTiO_3$ in certain aspects can be doped with Nb, where it substitutes on the Ti site (Kowalski, J. M., et al., Ceram. Intl. 7:55-59, 1981). For every $Nb^{5+}$ that is added to the lattice, one adjacent Ti atom changes its valence state to +3 (Chan, N. H., J. Electrochem. Soc. 128:1762-1769, 1981; Aukland, N., et al., J. Mater. Res. 19: 1723-1729, 2004). The present inventors have found in some aspects of the present teachings that doping $SrTiO_3$ with Nb can confer similar enhancement of antioxidant properties as Nb-doped $TiO_2$.

In some aspects, the present inventors observed that $BaTiO_3$ can be, in both the neutrophil and cell-free systems, a more effective catalyst than $SrTiO_3$. In some aspects, both materials can have similar surface compositions where the surface is terminated by BaO and $TiO_2$ for $BaTiO_3$, and SrO and $TiO_2$ for $SrTiO_3$. However, $BaTiO_3$ can be more prone to defects than $SrTiO_3$ (Lo, W. J., et al., Surface Science 71: 199-219, 1978). This is consistent with our hypothesis that the antioxidant properties of the titanium oxide surfaces are enhanced by increased surface defects.

In some embodiments, a titanium oxide defect having antioxidant activity can further comprise a dopant having a +5 valence state. Hence, many metal ions can serve as dopants having a +5 valence state. Some non-limiting examples of dopants which can be comprised by Ti(III)-containing defects in a titanium oxide include vanadium, niobium, tantalum, chromium, molybdenum, tungsten, manganese, rhenium, ruthenium, iridium, and a combination thereof. In particular, niobium can be a dopant for titanium oxides for the anti-oxidizing materials of the present teachings.

Other embodiments of the present teachings include crystalline titanium alloys which can have crystalline structures that include defects which can catalyze destruction of reactive oxygen species. These alloys can also comprise Ti(III)-containing defects which can catalyze destruction of ROS.

In various configurations, X-ray Photoelectron Spectroscopy (XPS) can be used to measure Ti(III) content, as well as content of other ions, of a biomaterial of the present teachings. See, e.g., Practical Surface Analysis-Auger and X-ray Photoelectron Spectroscopy, D. Briggs and M. P. Seah (Editors), Wiley Interscience, 1990 (2nd ed.); Photoelectron Spectroscopy (Springer Series in Solid-State Sciences Vol. 82), S. Huefner, Springer Verlag, 1995; Introduction to Photoelectron Spectroscopy (Chemical Analysis Vol. 67), P. K. Ghosh, Wiley Interscience, 1983; Handbook of Monochromatic XPS Spectra—Vol. 1—The Elements and Native Oxides, B. V. Crist, XPS International, Inc., 1999; Modern ESCA—The Principles and Practice of X-ray Photoelectron Spectroscopy, T. L. Barr, CRC, 1994; Handbook of X-ray Photoelectron Spectroscopy, J. Moulder, William F. Stickle, P. E. Sobol, and K. D. Bomben, (J. Chastain, editor) Perkin Elmer Corporation (Physical Electronics), 1992 (2nd edition).

In some non-limiting examples, a crystalline titanium alloy can be $SrTiO_3$ or $BaTiO_3$. Furthermore, in some aspects, a crystalline titanium alloy can comprise a perovskite crystal structure. In addition, in some configurations, a crystalline titanium alloy can further comprise a dopant. In some configurations, a dopant can enhance the anti-oxidant activity of the alloy. Some non-limiting examples of dopants which can enhance anti-oxidant activity of a titanium alloy include vanadium, niobium, tantalum, chromium, molybdenum, tungsten, manganese, rhenium, ruthenium, iridium, and a combination thereof. In some aspects, the titanium alloy can be $SrTiO_3$ and the dopant can be niobium, or the titanium alloy can be $BaTiO_3$ and the dopant can be niobium.

In various embodiments, a titantium alloy of the present teachings can comprise anatase crystals, rutile crystals, or a combination thereof. These crystal structures can also, in some configurations, comprise defects which can provide catalytic sites which can destroy oxidative species. These catalytic sites are believed to comprise Ti(III) and do not require a dopant.

In various embodiments, a biocompatible implant comprising a surface comprising a crystalline titanium oxide having defects comprising Ti(III) can be a biomedical device, such as, in non-limiting example, a heart valve, a prosthesis of the abdominal aorta, an artificial polymeric vessel, an artificial articulation, a medical sewing material, a wound dressing, an adhesion material, a polymeric bone implant, an artificial skin implant, an adsorbent, or a pharmacological microcapsule.

In various embodiments of the present teachings, the inventors set forth methods of coating an implant with a biocompatible surface. These methods include subjecting a surface comprising titanium to anodic spark deposition, wherein the surface breaks down reactive oxygen species, such as peroxynitrite, at a greater rate after the anodic spark deposition compared to the surface prior to the anodic spark deposition. Measuring the breakdown rate of peroxynitrate can be accomplished using the methods well known to skilled artisans, such as the methods described in the Examples herein. In addition, in various embodiments, titanium can be deposited on the surface of a biocompatible implant using methods well known to skilled artisans, such as, for example, chemical vapor deposition techniques, including plasma-enhanced chemical vapor deposition techniques (Schropp, R. E.

I, et al., Materials Physics and Mechanics 1: 73-82, 2000; Jaeger, R. C., "Film Deposition", in: Introduction to Microelectronic Fabrication. Upper Saddle River: Prentice Hall, 2002. ISBN 0-201-44494-7).

In various aspects, a biocompatible surface formed by the methods can further comprise a dopant, which can be a metal such as those listed herein, in particular niobium. Furthermore, in some aspects, a surface comprising titanium can comprise titanium oxide ($TIO_2$). In yet other aspects, the methods can be used to form a titanium oxide which further comprises a metal, such as barium or strontium.

In various configurations, such combinations of titanium oxide with a metal can be comprised by perovskite crystals, which can be formed using anodic spark deposition. In some configurations, a perovskite crystal can comprise the titanium, the oxygen and the metal in stoichiometric ratios. In addition, in some configurations, a perovskite titanate can further comprise a dopant, such as a metal dopant as set forth herein, and can be a metal having a valence of +5. In some configurations, the dopant can be niobium.

In yet other configurations, the present methods can yield a biocompatible implant having a surface comprising titanium oxide in the form of a rutile titanate, an anastase titanate, or a combination thereof. Such titanates can comprise defects which render them effective for destroying oxidants, and can be formed using anodic spark deposition. In yet other configurations, one or more dopants can be introduced to a surface, thereby forming a rutile titanate, an anastase titanate, or a combination thereof comprising a dopant.

The present teachings provide methods and compositions which increase the biocompatibility of titanium alloys. These methods use processes that induce formation of particular crystal structures, and oxidation techniques for forming electron doped titanium oxide and perovskite films. The present teachings are directed to coatings and layers, devices, implants and other surfaces adapted to be implanted within a human body, or to be in contact with one or more tissues susceptible to inflammatory response, as well as methods for making such devices. Non-limiting examples of such coatings, layers, devices and implants include heart valves, prostheses of the abdominal aorta, artificial polymeric vessels, artificial articulations, medical sewing materials, wound dressings, adhesion materials, polymeric bone implants, artificial skin implants, adsorbents, oxygen carriers, microcapsule polymeric materials for pharmacology, viscoelastic materials, bioadhesion materials and tooth crowns. As used herein, the term implantable device can include a partially implanted device such as, for example, an ophthalmic lens or a contact lens for correcting vision. In addition to implant devices, storage containers and surfaces in which tissue is contacted can be coated with materials of the present teachings to prevent degradation of the tissue due to inflammatory or other responses to superoxide ($O_2$) or other oxidants.

The present teachings disclose using anodic spark deposition (ASD) and electron doping to enhance the biocompatibility of titanium coated implants. In some embodiments of the present teachings, a medical implant can be coated on at least a portion of a surface with a biocompatible layer deposited by ASD. In various aspects, a coating produced by ASD can be thicker than a natural oxide layer that can form on the surface of many of metals used in implant technology, such as titanium.

The present teachings are also directed to surfaces that are coated with a layer of electron doped titanium oxide, perovskite titanate, or electron doped perovskite titanate.

In some embodiments, the present teachings disclose using the biomaterials described herein not only as implants, but also as surfaces for the culturing of tissue and/or cell samples, as well as components of containers used for the storage of biological material. In some aspects, such surfaces and containers can be completely inert with regard to any immunological functions retained by the tissue/cell samples. Accordingly, in some aspects, the teachings include methods of culturing tissues and cells. In various aspects, these methods comprise culturing and/or storing a tissue or cell culture in a container comprising a biomaterial described herein.

ASD can provide the extra energy to form crystalline phases of an oxide. In some embodiments, phases of titanium oxide can be anatase and rutile.

The phenomenon of metal transfer by short duration electric discharge is well-known. It is believed that metal melted due to the high temperature of a spark can be transferred from an electrode to a surface via an expanding gas bubble. Generally, maximum material transfer is made when the counter-electrode is the anode and the surface to be coated is the cathode of a discharge circuit.

Anodic oxidation and anodic spark discharge (ASD) are essentially the same processes with the exception that ASD takes place at high applied potentials where the dielectric breakdown of the oxide layer occurs. Titanium, for example, forms a natural oxide layer upon exposure to air and is mainly composed of $TiO_2$. The thickness of the $TiO_2$ layer ranges from 5 to 10 nm depending on the temperature and humidity.

In various configurations of the present teachings, ASD can produce a titanium oxide layer ranging from 200 to 300 nm.

Anodic oxidation can be effected by placing a titanium metal sheet, for example, in an electrolytic cell. The bath of the electrolytic cell can provide good conductivity between the titanium sheet and the counter electrode. $H_2SO_4$ is a common choice for an electrolyte in such cells. In these cells, a titanium metal can be held at a potential positive to the counter electrode, which is usually composed of either platinum or silver chloride.

In anodic oxidation, an electrode reaction in combination with electric-field-driven metal and oxygen ion diffusion can lead to the formation of an oxide film at the surface of the titanium sheet. The oxide surface can be in contact with the electrolyte, which can be in contact with the anode. The main reactions of anodic oxidation can be represented by the following reaction schemes:

At the $Ti/TiO_2$ interface: $Ti \rightarrow Ti^{2+} + 2e^-$

The applied electric filed led to the formation of the oxide: $Ti^{2+} + 2O_2^- \rightarrow TiO_2 + 2e^-$.

The oxide can keep growing as long as the electric field is strong enough to drive the ions through the film. The thickness will be approximately linearly dependent on the applied voltage until the dielectric breakdown voltage is reached (between 100 to 160 volts for $TiO_2$). There is a range in the value of the breakdown voltage because of the non-uniformity of the oxide film. Defects, areas of concentrated stress and non-uniform thickness, can be randomly spread throughout the surface, making the potential voltage drop across the surface non-uniform. When the applied voltage increases past the breakdown voltage, the voltage drop at these weak points exceeds the dielectric strength of the layer. An extremely high concentration of current flows through these small areas, at which time sparks can be seen across the surface. Anions are strongly attracted by the high intensity of the electric discharge at the metal-anodic interface, which highly accelerates the deposition of material through the sparking process. The temperature can vary from 2000 to 8000 K at these localized points, temperatures which are easily larger than the melting temperatures of the metal. Molten spots can and have been observed. Although the localized temperatures are high, there is rapid cooling by the bath.

In some aspects of the present teachings, ASD can also be used to form perovskites such as $BaTiO_3$. In this case, the difference from the above process is that the electrolyte used is $Ba(OH) \cdot 8H_2O$. This electrolyte allows for the initial growth of $TiO_2$ but also provides the reaction cation, $Ba^{2+}$. The solid state reaction between $Ba^{2+}$ and $TiO_2$ takes place when the breakdown voltage is reached. The reaction is initiated by the spark discharges which provide the necessary energy to form the perovskite structure of $BaTiO_3$. Other factors such as pH, temperature and current density can also have an effect on the oxide layer formed.

An electrolyte used in the present teachings can be any other electrolyte capable of donating a cation to the perovskite structure of crystals comprising the metal surface, such as, in non-limiting example, $Ca(OH)_2$. In some embodiments, anode spark deposition can be used to form $CaTiO_3$. In addition to calcium, an electrolyte can comprise one or more cations such as, for example barium or strontium ions.

Some embodiments of the present teachings include perovskite coatings. In various aspects, ASD can be used on a surface comprising a titanium alloy in the presence of an electrolyte such as barium hydroxide or calcium hydroxide. The resultant perovskite crystals may be electron doped or undoped, depending on the nature of the underlying titanium alloy.

In various configurations, a biocompatible implant coated using ASD does not have to be planar; a surface of any shape can be coated.

EXAMPLES

Aspects of the present teachings may be further understood in light of the following examples, which should not be construed as limiting the scope of the present teachings in any way.

Example 1

Niobium Doped $TiO_2$ Reduced Peroxynitrite Concentration

Figure 3:
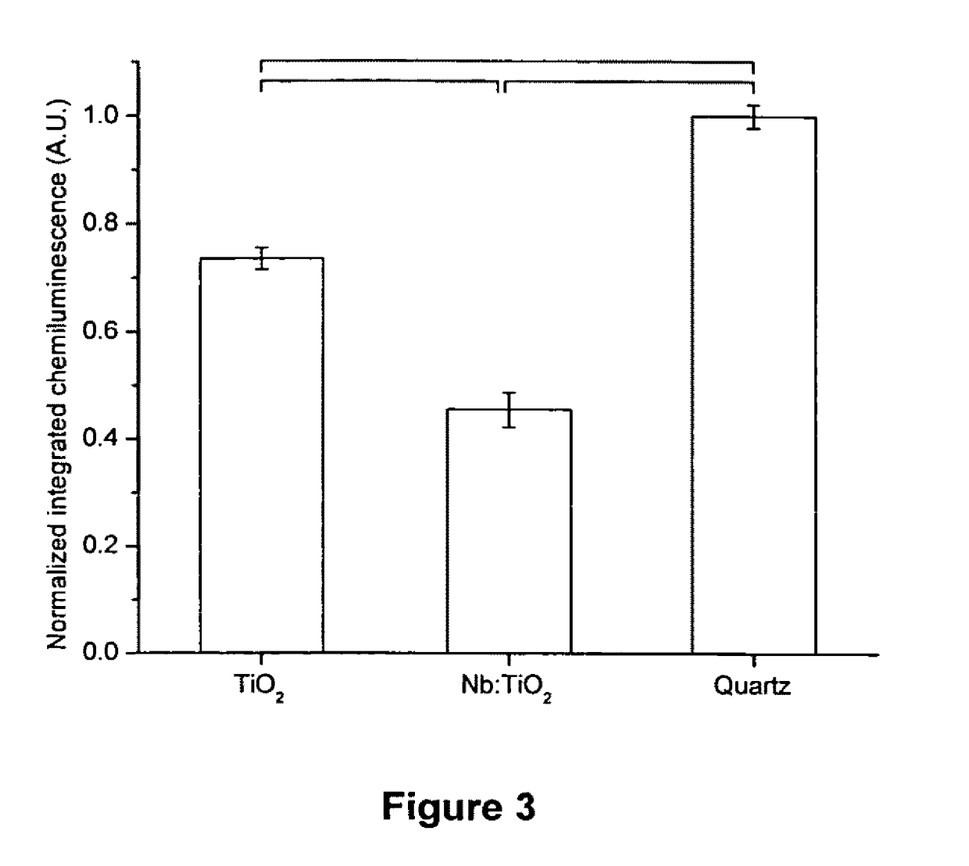
FIG. 3. Reactive oxygen species (ROS) were produced by the peroxynitrite donor 3-morpholinosydnonimine-N-ethylcarbamide (SIN-1; Cayman Chemical, Ann Arbor, Mich.) and were measured as integrated chemiluminescence over a 20 minute period at 37 .degree. C. The signals were normalized to that of the quartz sample. The brackets indicate significant difference ($p<0.05$) between groups. Niobium (Nb) doped $TiO_2$ reduces the concentration of peroxynitrite.

An in vitro assay used SIN-1 as a donor of peroxynitrite. Peroxynitrite concentration was measured as integrated chemiluminescence over a twenty minute period at 37 .degree. C. FIG. 3 shows that niobium doped $TiO_2$ reduced the concentration of peroxynitrite. (FIG. 3).

Example 2

Perovskite Titanates Reduced Peroxynitrite Concentration More than $TiO_2$

Figure 4:
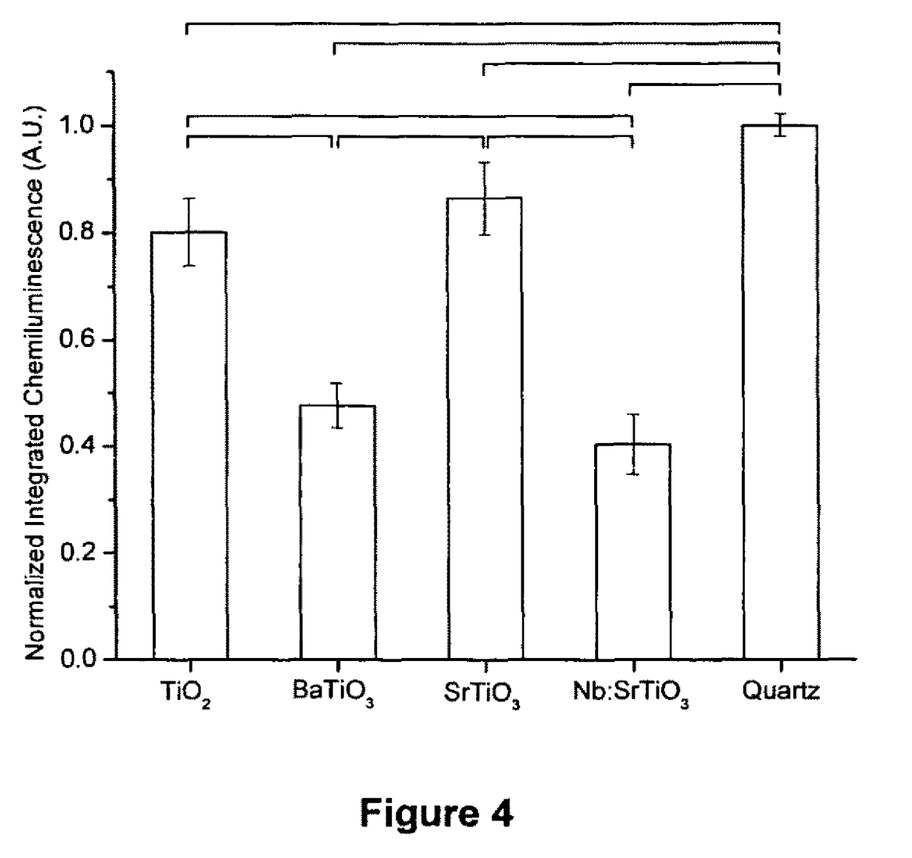
FIG. 4. Reactive oxygen species (ROS) were produced by peroxynitrite donor SIN-1 and was measured as integrated chemiluminescence over a 20 minute period at 37 .degree. C.

Reactive oxygen species were produced by peroxynitrite donor SIN-1. Peroxynitrite concentration was measured as integrated chemiluminescence over a twenty minute period. The assay was conducted at 37 .degree. C. FIG. 4 shows that $BaTiO_3$ and Nb—$SrTiO_3$ were better at reducing the concentration of peroxynitrite than $TiO_2$.

Example 3

Figure 5:
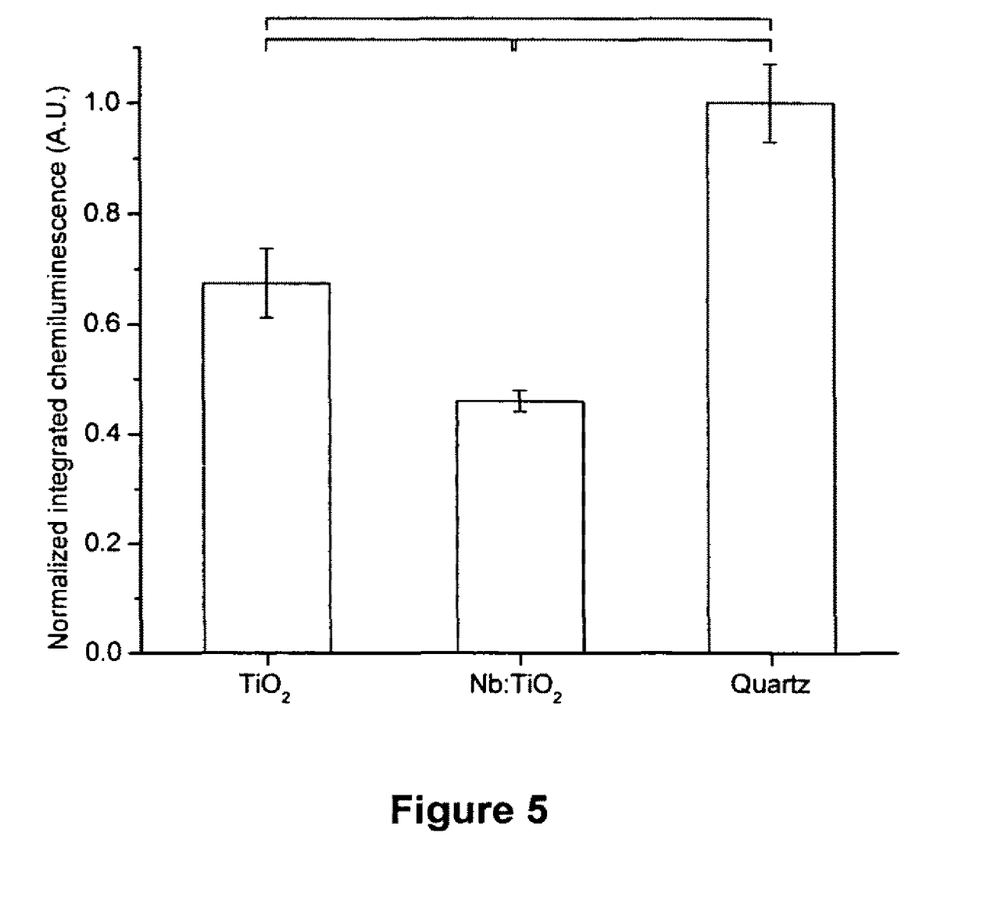
FIG. 5. Reactive oxygen species were produced by surface-adhering neutrophils and was measured as integrated chemiluminescence over a 20 minute period at 37 .degree. C. The signals were normalized to that of the quartz sample. The brackets indicate significant difference ($p<0.05$) between groups. The ability to break down superoxide produced by the neutrophils cells is improved by doping $TiO_2$ with niobium (Nb).
Figure 6:
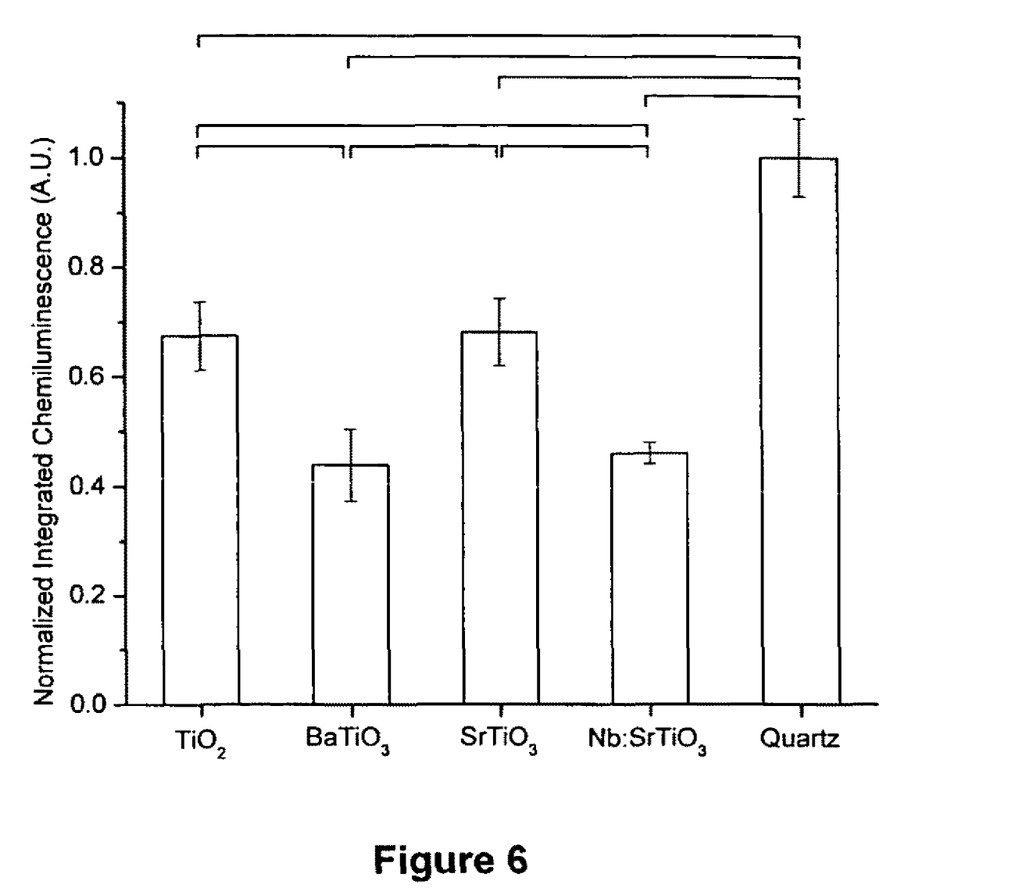
FIG. 6. Reactive oxygen species were produced by surface-adhering neutrophils and was measured as integrated chemiluminescence over a 20 minute period at 37 .degree. C. The signals were normalized to that of the quartz sample. The brackets indicate significant difference ($p<0.05$) between groups. Anti-oxidant properties of $BaTiO_3$ and niobium (Nb) doped $SrTiO_3$ are better than $TiO_2$.

Neutrophil-Generate Reactive Oxygen Species were Reduced by Niobium Doped $TiO_2$ and Perovskite Titanates Surface adhering neutrophils produced reactive oxygen species that were measured as integrated chemiluminescence over a twenty minute period. The signals were normalized to that of the quartz sample. FIG. 5 and FIG. 6 show that the ability to break down superoxide produced by neutrophils cells was improved by doping $TiO_2$ with niobium (FIG. 5) or by using perovskite-doped titanates (FIG. 6).

Example 4

Anodizing and Anodic Spark Deposition Process

Anodizing and Anodic Spark Deposition are similar processes, with the difference being that anodic spark deposition takes place at high applied potentials where the dielectric breakdown of the oxide layer occurs.

Figure 1:
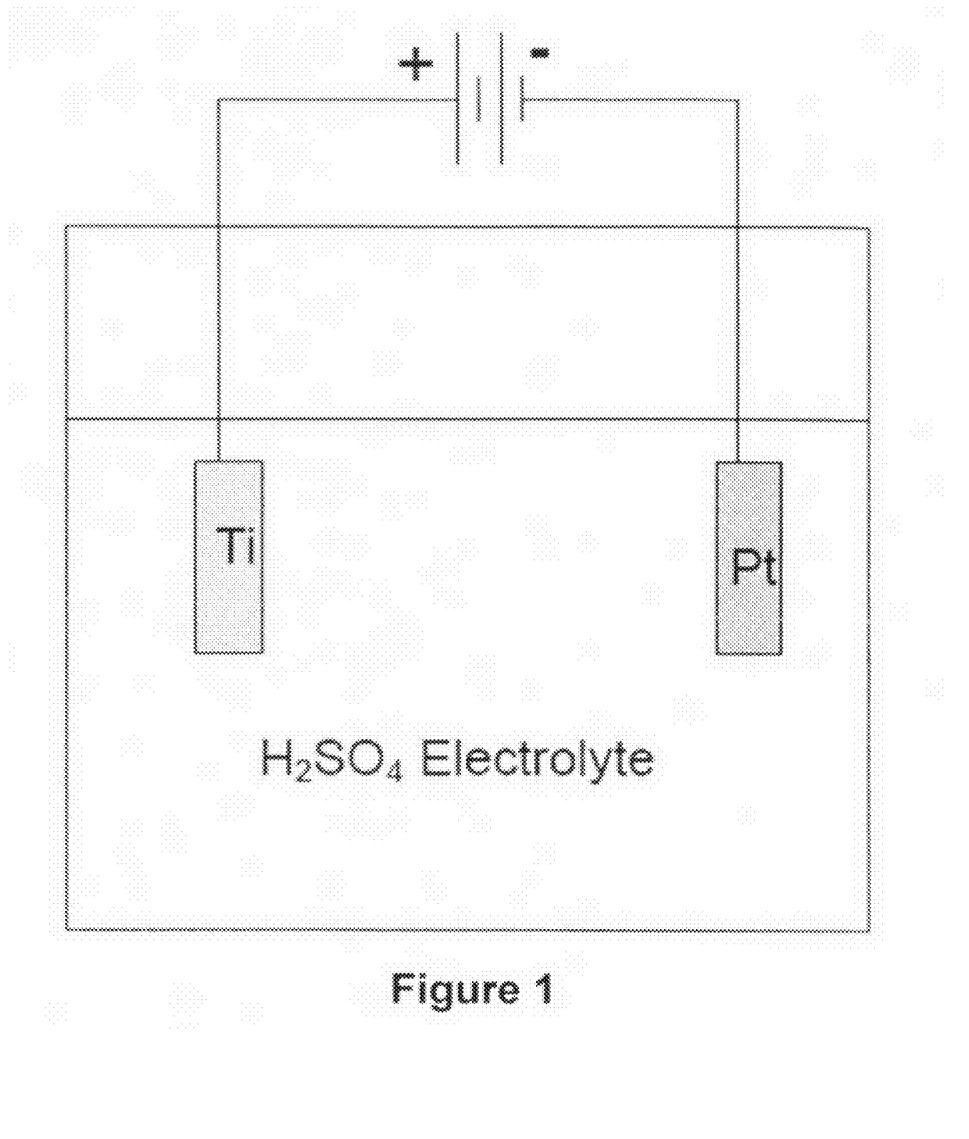
FIG. 1. The cathode is titanium metal and the anode is a platinum counter electrode. Both the cathode and anode are immersed in the electrolyte bath of $H_2SO_4$.
Figure 2:
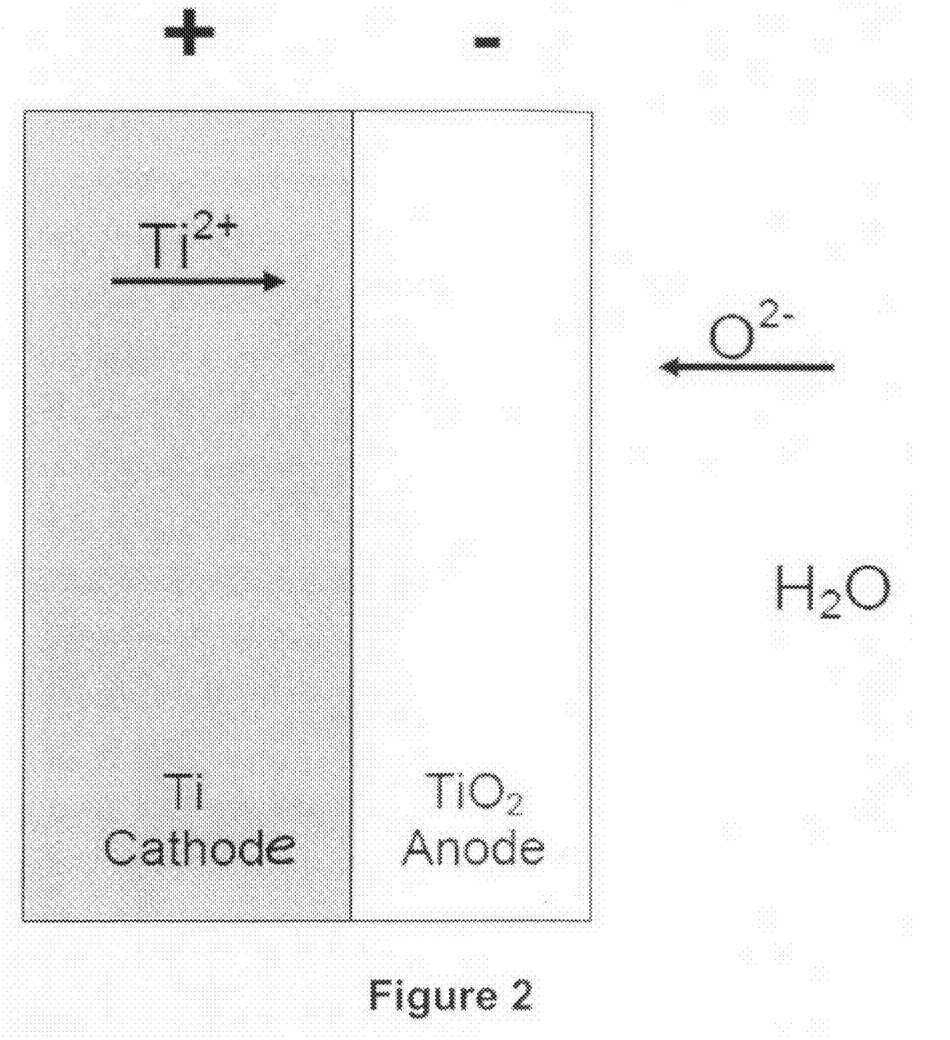
FIG. 2. The titanium metal is the cathode and the anode is the $TiO_2$ oxide layer because it is in contact with the electrolyte which is in contact with the platinum anode. The titanium and oxygen ions diffuse under the force of the electric field. When the ions meet they spontaneously form $TiO_2$.

A titanium sheet was placed in an electrolytic cell (see FIG. 1). The bath of the electrolytic cell contained an electrolyte that provided good conductivity between the titanium sheet and the counter electrode. $H_2SO_4$ was used as an electrolyte. The titanium metal was held at a positive potential relative to the counter electrode, which was composed of either platinum or silver chloride.

The electrode reactions in combination with electric field driven metal and oxygen ion diffusion led to the formation of an oxide film on the surface of the anode. The main reactions of anodic oxidation can be represented by the following reaction schemes:

At the $Ti/TiO_2$ interface: $Ti \rightarrow Ti^{2+} + 2e^-$

At the $TiO_2$/electrolyte interface: $2H_2O \rightarrow 2O^{2-} + 4H^+ \rightarrow 2H_2O \rightarrow O^{2-} + 4H^+ + 4e^-$ The applied electric filed led to the formation of the oxide: $Ti^{2+} + 2O_2^- \rightarrow TiO_2 + 2e^-$.

The oxide kept growing as long as the electric field was strong enough to drive the ions through the film, with the thickness almost linearly dependent on the applied voltage.

When the dielectric break down voltage was reached (about 100 to 160 volts for $TiO_2$), areas of concentrated stress and non-uniform thickness in the film randomly spread throughout the surface, making the potential voltage drop across the surface non-uniform.

Other Embodiments

The detailed description set-forth above is provided to aid those skilled in the art in practicing the present teachings. Equivalent embodiments are intended to be within the scope of these teachings. Indeed, various modifications in addition to those shown and described herein will become apparent to those skilled in the art from the foregoing description which do not depart from the spirit or scope of the present teachings. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present teachings. Publications incorporated herein by reference in their entirety include:

1. Leventhal, G. S., Titanium, a metal for surgery. Journal of Bone and Joint Surgery, 1951. 33-A(2): p. 473-4.
2. Leventhal, G. S., Titanium for femoral head prosthesis. The American Journal of Surgery, 1957. 94(5): p. 735-40.
3. Bothe, R. T., L. E. Beaton, and H. A. Davenport, Reaction of bone to multiple metallic implants. Surgery, Gynecology & Obstetrics, 1940. 71: p. 598-602.
4. Wang, K., The use of titanium for medical applications in the USA. Materials Science & Engineering A-Structural Materials Properties Microstructure & Processing, 1996. 213(1-2): p. 134-7.
5. Farivar, M. and P. Sioshansi, Metallized polymeric implant with ion embedded coating, in U.S. Pat. No. 5,468,562. 1995, Spire Corporation, Bedford, Mass.: USA.
6. Olsson, K., L. Jianguo, and U. Lindgren, Composition, manufacturing, and use of silicon nitride as a biomatierial for medical purpose, in WO9947471. 1999: Sweden.
7. von Realm, A. F. and F. W. Cooke, Method for promoting tissue adhesion to soft tissue implants, in U.S. Pat. No. 4,846,834. 1989, Clemson University, Clemson, S.C.: USA.
8. Babizhayev, M. A., Coated ophthalmic and implantable devices and methods for producing same, in U.S. Pat. No. 6,613,088 B1. 2003: Russia.
9. Albrektsson, T., P. I. Branemark, H. A. Hansson, B. Kasemo, K. Larsson, I. Lundstrom, D. H. McQueen, and R. Skalak, The interface zone of inorganic implants in vivo: Titanium implants in bone. Annals of Biomedical Engineering, 1983. 11: p. 1-27.
10. Johansson, A., J. U. Lindgren, C. E. Nord, and O, Svensson, Material and design in haematogenous implant-associated infections in a rabbit model. Injury, 1999. 30(10): p. 651-7.
11. Glowinski, J., R. Farbiszewski, S. Glowinski, and M. Chwiecko, Activity and distribution of superoxide dismutase in the layers of polyester grafts. European surgical research, 1997. 29(5): p. 368-74.
12. Hukkanen, M., S. A. Corbett, J. Batten, Y. T. Konttinen, I. D. McCarthy, J. Maclouf, S. Santavirta, S. P. Hughes, and J. M. Polak, Aseptic loosening of total hip replacement. Macrophage expression of inducible nitric oxide synthase and cyclo-oxygenase-2, together with peroxynitrite formation, as a possible mechanism for early prosthesis failure. The Journal of Bone & Joint Surgery (Br), 1997. 79(3): p. 467-74.
13. Hukkanen, M., S. A. Corbett, L. A. Platts, Y. T. Konttinen, S. Santavirta, S. P. Hughes, and J. M. Polak, Nitric oxide in the local host reaction to total hip replacement. Clinical Orthopaedics and Related Research, 1998(35): p. 53-65.
14. Misko, T. P., M. K. Highkin, A. W. Veenhuizen, P. T. Manning, M. K. Stern, M. G. Currie, and D. Salvemini, Characterization of the cytoprotective action of peroxynitrite decomposition catalysts. The Journal of Biological Chemistry, 1998. 273(25): p. 15646-53.
15. Salvemini, D., D. P. Riley, P. J. Lennon, Z. Q. Wang, M. G. Currie, H. Macarthur, and T. P. Misko, Protective effects of a superoxide dismutase mimetic and peroxynitrite decomposition catalysts in endotoxin-induced intestinal damage. British Journal of Pharmacology, 1999. 127(3): p. 685-92.
16. Cuzzocrea, S., T. P. Misko, G. Costantino, E. Mazzon, A. Micali, A. P. Caputi, H. Macarthur, and D. Salvemini, Beneficial effects of peroxynitrite decomposition catalyst in a rat model of splanchnic artery occlusion and reperfusion. FASEB Journal, 2000. 14(9): p. 1061-72.
17. Suzuki, R. and J. A. Frangos, Inhibition of inflammatory species by titanium surfaces. Clinical Orthopaedics and Related Research, 2000(372): p. 280-9.
18. Bjursten, L. M. and J. A. Frangos, Material for Implantation, in US 20050074602A1. 2005: US.
19. Kurze, P., D. Banerjee, and H. J. Kletke, Method of producing oxide ceramic layers on barrier layer-forming metals and articles producing by the method, in U.S. Pat. No. 5,385,662. 1995, Electro Chemical Engineering GmbH: Germany.
20. Beauvir, J., Oxidizing electrolytic method for obtaining a ceramic coating at the surface of a metal, in U.S. Pat. No. 6,808,613 B2. 2004: France.
21. Tran Bao, V., S. D. Brown, and G. P. Wirtz, Mechanism of anodic spark deposition. American Ceramic Society Bulletin, 1977. 56(6): p. 563-6.
22. Marchenoir, J. C., J. P. Loup, and J. Masson, The study of porous layers formed by anodic oxidation of titanium under high voltage. Thin Solid Films, 1980. 66(3): p. 357-69.
23. Miller, D., S. Mamiche-Afara, M. J. Dignam, and M. Moskovits, The photoactivity of porous $TiO_2$ anodized at a high voltage. Chemical Physics Letters, 1983. 100(3): p. 236-40.
24. Meyer, S., R. Gorges, and G. Kreisel, Preparation and characterisation of titanium dioxide films for catalytic applications generated by anodic spark deposition. Thin Solid Films, 2004. 450(2): p. 276-81.
25. Khoo, S. W., G. C. Wood, and D. P. Whittle, Analysis of anodic oxide films on alloys. Electrochimica Acta, 1971. 16(10): p. 1703-1717.
26. Aladjem, A., Anodic oxidation of titanium and its alloys. Journal of Materials Science, 1973. 8(5): p. 688-704.
27. Chiesa, R., E. Sandrini, M. Santin, G. Rondelli, and A. Cigada, Osteointegration of titanium and its alloys by anodic spark deposition and other electrochemical techniques: a review. Journal of Applied Biomaterials and Biomechanics, 2003. 1(2): p. 91-107.
28. Schlottig, F., D. Dietrich, J. Schreckenbach, and G. Marx, Electron microscopic characterization of $SrTiO_3$ films obtained by anodic spark deposition. Fresenius Journal of Analytical Chemistry, 1997. 358(1-2): p. 105-7.
29. Wu, Z. and M. Yoshimura, Investigations on procedures of the fabrication of barium titanate ceramic films under hydrothermal-electrochemical conditions. Solid State Ionics, 1999. 122(1-4): p. 161-72.
30. Wu, C.-T. and F.-H. Lu, Electrochemical deposition of barium titanate films using a wide electrolytic voltage range. Thin Solid Films, 2001. 398-399: p. 621-625.
31. Lu, F.-H., C.-T. Wu, and C.-Y. Hung, Barium titanate films synthesized by an anodic oxidation-based electrochemical method. Surface and Coatings Technology, 2002. 153(2-3): p. 276-283.
32. Rachmilewitz, D., J. S. Stamler, F. Karmeli, M E Mullins, D J Singel, J. Loscalzo, R J Xavier, and D K Podolsky. Peroxynitrite-induced rat-colitis—a new model of chronic inflammation. 1993. Gastroenterology 105(6):1681-8.
33. Salvemini, D., Z Wang, D. Bourdon, M. Stern, M. Currie, and P. Manning. Evidence of peroxynitrite involvement in the carrageenan-induced rat paw edema 1996. European Journal of Pharmacology, 303(3): 217-20

What is claimed is:

1. An implant comprising a biocompatible material comprising two or more layers where one layer is provided at a surface of the implant and comprising a crystalline titanium oxide having defects comprising Ti(III) comprises of a titanium alloy selected from the group consisting of $SrTiO_3$ and $BaTiO_3$.

2. The implant in accordance with claim 1, wherein the crystalline titanium oxide having a defect comprising Ti(III) further comprises a dopant selected from the group consisting of vanadium, niobium, tantalum, chromium, molybdenum, tungsten, manganese, rhenium, ruthenium, iridium, and a combination thereof.

3. The implant in accordance with claim 2, wherein the dopant is niobium.

4. The implant in accordance with claim 1, wherein the titanium alloy further comprises a dopant selected from the group consisting of vanadium, niobium, tantalum, chromium, molybdenum, tungsten, manganese, rhenium, ruthenium, iridium, and a combination thereof.

5. The implant in accordance with claim 1, wherein the $SrTiO_3$ is niobium-doped $SrTiO_3$.

6. The implant in accordance with claim 1, wherein the crystalline titanium oxide further comprises a perovskite crystal structure.

7. The implant in accordance with claim 1, wherein the crystalline titanium oxide comprises an anatase crystal structure.

* * * * *

UNITED STATES PATENT AND TRADEMARK OFFICE
CERTIFICATE OF CORRECTION

PATENT NO. : 7,910,221 B2  
APPLICATION NO. : 11/672867  
DATED : March 22, 2011  
INVENTOR(S) : Ramiro Contreras, Herman Sahlin and John A. Frangos Page 1 of 1

It is certified that error appears in the above-identified patent and that said Letters Patent is hereby corrected as shown below:

Replace the Statement of Government Interest after the Title with the following:

--STATEMENT OF GOVERNMENT INTEREST

This invention was made with government support under Grants EB000823 and AR47032 awarded by the National Institutes of Health. The government has certain rights in the invention--

Signed and Sealed this  
Third Day of January, 2012

David J. Kappos  
*Director of the United States Patent and Trademark Office*